United States Patent
Welsh et al.

(10) Patent No.: US 12,179,037 B2
(45) Date of Patent: Dec. 31, 2024

(54) RADIOTHERAPIES AND USES THEREOF

(71) Applicant: Board of Regents, The University of Texas System, Austin, TX (US)

(72) Inventors: James Welsh, Houston, TX (US); Maria Angelica Cortez, Houston, TX (US); David Hong, Houston, TX (US); Hampartsoum Berj Barsoumian, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 349 days.

(21) Appl. No.: 17/312,802

(22) PCT Filed: Dec. 9, 2019

(86) PCT No.: PCT/US2019/065246
§ 371 (c)(1),
(2) Date: Jun. 10, 2021

(87) PCT Pub. No.: WO2020/123388
PCT Pub. Date: Jun. 18, 2020

(65) Prior Publication Data
US 2022/0062655 A1    Mar. 3, 2022

Related U.S. Application Data (60) Provisional application No. 62/778,009, filed on Dec. 11, 2018.

(51) Int. Cl.
*A61N 5/10* (2006.01)
*A61K 35/17* (2015.01)
*C07K 16/28* (2006.01)

(52) U.S. Cl.
CPC ............... *A61N 5/10* (2013.01); *A61K 35/17* (2013.01); *C07K 16/2818* (2013.01)

(58) Field of Classification Search
CPC ....................................................... A61N 5/10
See application file for complete search history.

(56) References Cited

U.S. PATENT DOCUMENTS

| 4,870,287 A | 9/1989 | Cole et al. |
| 5,739,169 A | 4/1998 | Ocain et al. |
| (Continued) | | |

FOREIGN PATENT DOCUMENTS

| WO | WO 2016/109310 A1 | 7/2016 |
| WO | WO 2017/158116 A1 | 9/2017 |
| (Continued) | | |

OTHER PUBLICATIONS

Barsoumian, H. et al., "Low Dose Radiation Improves Anti-Tumor Responses in a Phase 2 Prospective Trial of Concurrent or Sequential Stereotactic Radiation and Ipilimumab in Patients with Metastatic Lesions," *Radiation Oncology*, 102.3 (2018): S26.

(Continued)

*Primary Examiner* — Hugh Maupin
(74) *Attorney, Agent, or Firm* — Parker Highlander PLLC (57) ABSTRACT

Provided are methods for sequential radiotherapies, such as XRT. In some embodiments, a higher dosage of an XRT may first be administered to a subject, optionally in combination with an immunotherapy, and subsequently a lower dosage XRT is administered to the subject to treat a cancer. Separating the dosage and intensity of the radiotherapies can be used to achieve improved therapeutic responses, such as improved anti-cancer responses, survival times, and/or abscopal effects.

105 Claims, 5 Drawing Sheets

(56) References Cited

U.S. PATENT DOCUMENTS

| | | | |
|---|---|---|---|
| 5,760,395 | A | 6/1998 | Johnstone |
| 5,801,005 | A | 9/1998 | Cheever et al. |
| 5,824,311 | A | 10/1998 | Greene et al. |
| 5,830,880 | A | 11/1998 | Sedlacek et al. |
| 5,843,398 | A * | 12/1998 | Kaminski ............. C07K 14/52 424/1.49 |
| 5,846,945 | A | 12/1998 | McCormick |
| 10,413,755 | B1 * | 9/2019 | Sahadevan ........... A61N 5/1042 |
| 2013/0261370 | A1 * | 10/2013 | Diaconescu ........... A61K 35/17 600/1 |
| 2014/0155678 | A1 * | 6/2014 | Zeng ....................... A61P 35/00 604/20 |
| 2014/0187845 | A1 * | 7/2014 | Diaconescu ........... A61K 35/17 600/1 |
| 2018/0154183 | A1 * | 6/2018 | Sahadevan .......... A61M 1/3615 |
| 2018/0280724 | A1 * | 10/2018 | Anderson ................ A61N 5/10 |
| 2020/0023195 | A1 * | 1/2020 | Anderson ................ A61N 5/10 |
| 2021/0221889 | A1 * | 7/2021 | Wang ................. C07K 16/2827 |
| 2021/0369782 | A1 * | 12/2021 | Agarwal ................ A61P 37/06 |
| 2022/0054550 | A1 * | 2/2022 | Smith ................ A61K 39/4631 |

FOREIGN PATENT DOCUMENTS

| | | | |
|---|---|---|---|
| WO | WO 2017/197259 | A1 | 11/2017 |
| WO | WO 2018/102786 | A1 | 6/2018 |
| WO | WO 2018/126277 | A1 | 7/2018 |
| WO | WO 2018/150326 | A1 | 8/2018 |
| WO | WO-2018183065 | A1 * | 10/2018 ............. A61K 45/06 |

OTHER PUBLICATIONS

Blankenbecler, R. et al., "Low-dose pretreatment for radiation therapy," *Dose-Response*, 8 (2010): 534-542.

Cai, J. et al., "Tumor-Associated Macrophages Derived TGF-β-Induced Epithelial to Mesenchymal Transition in Colorectal Cancer Cells through Smad2,3-4/Snail Signaling Pathway," *Cancer Res Treat.*, 51.1 (2019): 252-266.

Han, D. et al., "Comparison of once daily radiotherapy to 60 Gy and twice daily radiotherapy to 45 Gy for limited stage small-cell lung cancer," *Thoracic Cancer*, 6 (2015): 643-648.

Hu, Z. et al., "The Abscopal Effect of Radiation Therapy: What Is It and How Can We Use It in Breast Cancer?," *Curr Breast Cancer Rep.*, 9 (2017): 45-51.

Ngwa, W. et al., "Using immunotherapy to boost the abscopal effect," *Nat Rev. Cancer*, 18.5 (2018): 313-322.

PCT International Search Report and Written Opinion issued in International Patent Application No. PCT/US2019/065246, mailed Feb. 25, 2020.

PCT International Preliminary Report on Patentability, issued in International Patent Application No. PCT/US2019/065246, mailed Jun. 24, 2021.

"Radiation-immunotherapy combination can slow tumor growth for some patients with metastatic late-stage cancer," ASTRO, (2017): 1-8, https://markets.businessinsider.com/news/stocks/radiation-immunotherapy-combination-can-slow-tumor-growth-for-some-patients-with-metastatic-late , accessed Nov. 29, 2018.

"Radiation-immunotherapy combination can slow tumor growth for some patients with metastatic late-stage cancer," ASTRO, (2017): 1-4, https://www.astro.org/News-and-Publications/News-and-Media-Center/News-Releases/2017/Rdiation-immunotherapy-combination-can-slow-tumor, accessed Nov. 29, 2018.

"Radioimmunotherapy Active in Advanced Cancers," Medpage Today, (2017): 1-3, https://www.medpagetoday.com/meetingcoverage/astro/68116, accessed Nov. 29, 2018.

Verma, V. et al., "Safety of Combined Immunotherapy and Thoracic Radiation Therapy: Analysis of 3 Single-Institutional Phase I/II Trials," *International Journal of Radiation Oncology*, 101.5 (2018): 1141-1148.

* cited by examiner

RADIOTHERAPIES AND USES THEREOF

This application is a national phase application under 35 U.S.C. § 371 of International Application No. PCT/US2019/065246, filed Dec. 9, 2019, which claims the benefit of U.S. Provisional Patent Application No. 62/778,009, filed Dec. 11, 2018, the entirety of each of which is incorporated herein by reference.

BACKGROUND OF THE INVENTION

1. Field of the Invention

The present invention relates generally to the field of molecular biology and medicine. More particularly, it concerns radiotherapy methods, e.g., for the treatment of cancers.

2. Description of Related Art

Radiation therapy (XRT) has been widely used to control tumors locally by inducing nucleic acid damage and halting cell proliferation. XRT is presently used for local control of tumors, working by causing damage to tumor DNA, and typically can only be used to treat up to 1-3 sites of disease. Cancers, nonetheless, continue to present a significant clinical problem. Clearly, there is a need for new and improved therapies for the treatment of cancer.

SUMMARY OF THE INVENTION

The present invention is based, in part, on the discovery that lower doses of radiation can advantageously be used in combination therapies to treat a cancer. A lower dose radiation therapy may be administered in several different combination therapies. For example, a higher dose radiation can be used to kill one site of cancer (e.g., a primary tumor) helping to activate the immune cells, while a low dose radiation can be administered to other sites through the body (e.g., to secondary tumors) to bring in or attract these activated immune cells. Without wishing to be bound by any theory, the data supports the idea that high dose radiation therapy alone typically fails to benefit distant systemic sites because tumors often have an immune inhibitory barrier around them, typically referred to as the stroma. This stroma can prevent immune cells from penetrating into the tumor where the immune cells could kill the cancer. Provided herein are methods that utilize low dose radiation to distant tumor sites in order to disrupt this inhibitory stroma, and this low dose radiation therapy may allow or promote penetration of the immune cells through the stroma and into the tumor. Thus, in some embodiments, a low dose radiation therapy may be administered in combination with a higher dose radiation therapy and/or an immunotherapy. In some embodiments, the low dose radiation is delivered at the same time or after the high dose radiation. The low dose radiation may advantageously be administered in combination with or in the presence of a checkpoint therapy (e.g., an anti-CTLA-4 or anti-PD1/PDL1 therapy) since these drugs can help improve to effectiveness of immune cells. In some embodiments, a combination of higher dose radiation plus low dose radiation to other sites (e.g., secondary tumors) along with immunotherapy is administered to a patient to treat a cancer. Without wishing to be bound by any theory, the data supports the idea that a low dose radiation therapy may modulate tumor stroma to reduce the ability of tumors to evade the immune response.

In some embodiments, repeated administrations of radiotherapies that differ in dosage can provide significant improvements for the treatment of a cancer such as, e.g., improved survival and/or beneficial abscopal effects. In some embodiments, a low dose radiotherapy (e.g., a subclinical dose of 20-160 cGy per fraction, which is less than the dose is currently used for local control of a cancer) can be administered in combination with a separate high dose radiotherapy (e.g., XRT ranging from about 20 Gy in 5 fractions to about 50 Gy in 4 fractions). The higher dose radiotherapy may be administered before or after the lower dose radiotherapy. In some embodiments, the high dose radiotherapy is administered to a subject before the lower dose radiotherapy. Due to possible beneficial immune effects that may result from the radiotherapy, in some embodiments the radiotherapy is administered to a subject in combination with a second anti-cancer treatment such as, e.g., an immunotherapy. Without wishing to be bound by any theory, the data provided in the below examples is consistent with the idea that tumors exposed to the low dose radiotherapy may be "opened up" and/or become more vulnerable and accessible to immune cells. The low dose radiotherapy may thus significantly improve current immunotherapies such as, e.g., checkpoint inhibitor therapies such as anti-PD1 immunotherapies, anti-CTLA-4 immunotherapies, and/or engineered cell therapies such as CAR-T cells.

As shown in the below examples, it was observed that treating transplanted tumors in mice at one site with stereotactic high dose radiotherapy (XRT) followed by non-ablative low dose XRT directed towards other systemic tumor sites significantly reduced the growth of secondary tumors and limited metastasis. In a clinical trial, patients with several tumor masses at different sites of the same lung were included. The inventors observed that treating one site with high stereotactic XRT lead to the shrinkage of another nearby tumor that was left untreated but unintentionally received scattered low dose radiation. Other tumor sites analyzed in the vicinity that were out of the low dose radiation zone did not shrink and their growth was not affected. This technology can be combined with several immunotherapeutic approaches, such as anti-PD1, anti-PD-L1, anti-CTLA-4, anti-TGF-0, OX40 agonists, 4-1BB agonists, IDO inhibitors, anti-GITR, anti-LAGS, anti-TIM3, anti-TIGIT, and anti-MERTK therapies. Additionally, the low dose XRT may be combined with cell therapies, like chimeric antigen expressing T-cells (CAR-T), T-cell receptors (TCR), natural killer cells (NK), or dendritic cells (DCs), which are effective in liquid tumors but are typically unable to penetrate into solid tumors due to stromal inhibitory barriers. The methods provided herein may be used to facilitate the expansion of XRT's role from local therapy to systemic immunological therapy. Without wishing to be bound by any theory, these results support the idea that the radiotherapies may promote beneficial immune modulation, shaping of the tumor microenvironment, and/or generation of systemic anti-tumor effects in a subject with a cancer.

An aspect of the present invention relates to a method of treating a cancer in a mammalian subject comprising administering a first radiotherapy to the subject, wherein the radiotherapy comprises a dose of from about 10 cGy to about 170 cGy per fraction, in combination with: (a) a second radiotherapy, wherein the second radiotherapy is a higher dose than the first radiotherapy, and/or (b) an immunotherapy. In various embodiments, the first radiotherapy may comprise about 10-190, 10-180, 10-170, 20-190, 20-180, 20-170, 10, 20, 30, 40, 50, 60, 70, 80, 90, 100, 110, 120, 130, 140, 150, 160, 170, 180 cGy per fraction or per day, or any range derivable therein. In some embodiments, the first radiotherapy is an external-beam radiation therapy (XRT). The first radiotherapy may comprise administering a dosage of 20-160 cGy per fraction or per day. The first radiotherapy may comprise administering a final dose of about 0.1-12 Gy, about 1-12 Gy, from about 2 Gy to about 12 Gy, or about 0.5-10 Gy. The first radiotherapy may comprise administering a final dose of about 1-9 Gy, or 1, 2, 3, 4, 5, 6, 7, 8, 9 Gy, or any range derivable therein. In some embodiments, the method further comprises administering the second radiotherapy. The second radiotherapy may comprise administering 1.8-2 Gy per fraction or per day. The second radiotherapy may comprise administering a final dose of from about 20 to about 80 Gy, or about 40-70 Gy; wherein the second radiotherapy is an external-beam radiation therapy (XRT). The second radiotherapy may comprise administering a final dose of from about 60 to about 70 Gy. The first radiotherapy may be administered to the subject after the second radiotherapy. In some embodiments, the first radiotherapy is administered to the subject from about 7 days to about 3 months, or from about 1-4 weeks after the second radiotherapy. The first radiotherapy may be administered to the subject before the second radiotherapy. In some embodiments, the first radiotherapy is administered to the subject from about 7 days to about 3 months, or from about 1-4 weeks before the second radiotherapy. The method may further comprise administering the immunotherapy to the subject. In some embodiments, the immunotherapy is an antibody or comprises an antibody variable domain. In some embodiments, the immunotherapy is a checkpoint inhibitor. In some embodiments, the immunotherapy is an anti-PD1 immunotherapy, an anti-PD-L1 immunotherapy, an anti-CTLA-4 immunotherapy, an anti-TGF-β, an OX40 agonist, a 4-1BB agonist, an IDO inhibitor, an anti-GITR immunotherapy, an anti-LAGS immunotherapy, an anti-TIM3 immunotherapy, an anti-TIGIT immunotherapy, or anti-MERTK immunotherapy, an intratumoral injection, a STING-targeted immunotherapy, a NLRP3-targeted immunotherapy, a TLR9-targeted immunotherapy, a CPG-targeted immunotherapy, a TLR4-targeted immunotherapy, a TLR7/8-targeted immunotherapy, a OX40-targeted immunotherapy, a MER-TK-targeted immunotherapy, an oncolytic virus immunotherapy, an anti-CTLA-4 immunotherapy, an anti-PD1 immunotherapy, an anti-PDL1 immunotherapy, an anti-CD40 immunotherapy, a FLT-3-ligand immunotherapy, or a IL-2 cytokine immunotherapy. In some embodiments, the immunotherapy is alemtuzumab, atezolizumab, ipilimumab, nivolumab, ofatumumab, pembrolizumab, or rituximab. In some embodiments, the immunotherapy is ipilimumab. The immunotherapy may comprise an engineered cell therapy or a cell therapy. The immunotherapy may comprise administering a chimeric antigen expressing T-cell (CAR-T), T-cell receptor (TCR), natural killer cell (NK), or dendritic cell (DC) therapy to the subject. In some embodiments, the immunotherapy is administered to the subject after the first radiotherapy. In some embodiments, the method further comprises administering a third anti-cancer therapy to the subject, wherein the third anti-cancer therapy is a chemotherapeutic, an intratumoral injection (e.g., an intratumoral immunotherapy), or a surgery. The method may further comprise administering a third anti-cancer therapy to the subject, wherein the third anti-cancer therapy is a chemotherapeutic or a surgery. In some embodiments, the first radiation therapy results in abscopal effects or systemic immune responses in the subject. The subject may be a human. In some embodiments, the cancer is in the lung, head, neck, abdomen, or pelvis. In some embodiments, the cancer is a lung cancer, a brain cancer, a breast cancer, a head and neck cancer, a cervical cancer, prostate cancer, a cancer of the eye, a liver cancer (e.g., hepatocellular carcinoma (HCC), intrahepatic cholangiocarcinoma, or hepatoblastoma), or a thyroid cancer.

In some embodiments, the methods further comprise administering the immunotherapy to the subject. The immunotherapy may be an antibody or may comprise an antibody variable domain. In some embodiments, the immunotherapy is a checkpoint inhibitor. In some embodiments, the immunotherapy is an anti-PD1 immunotherapy, an anti-PD-L1 immunotherapy, an anti-CTLA-4 immunotherapy, an anti-TGF-β, an OX40 agonist, a 4-1BB agonist, an IDO inhibitor, an anti-GITR immunotherapy, an anti-LAGS immunotherapy, an anti-TIM3 immunotherapy, an anti-TIGIT immunotherapy, an anti-MERTK immunotherapy, an intratumoral injection, a STING-targeted immunotherapy, a NLRP3-targeted immunotherapy, a TLR9-targeted immunotherapy, a CPG-targeted immunotherapy, a TLR4-targeted immunotherapy, a TLR7/8-targeted immunotherapy, a OX40-targeted immunotherapy, a MER-TK-targeted immunotherapy, an oncolytic virus immunotherapy, an anti-CTLA-4 immunotherapy, an anti-PD1 immunotherapy, an anti-PDL1 immunotherapy, an anti-CD40 immunotherapy, a FLT-3-ligand immunotherapy, or a IL-2 cytokine immunotherapy. In some embodiments, the immunotherapy is alemtuzumab, atezolizumab, ipilimumab, nivolumab, ofatumumab, pembrolizumab, or rituximab. In some embodiments, the immunotherapy is ipilimumab. In some embodiments, the immunotherapy comprises an engineered cell therapy or a cell therapy. The immunotherapy may comprise administering a chimeric antigen expressing T-cell (CAR-T), T-cell receptor (TCR), natural killer cell (NK), or dendritic cell (DC) therapy to the subject. The immunotherapy may be administered to the subject after or before the first radiotherapy. The method my further comprise administering an engineered cell therapy or a cell therapy to the subject. The engineered cell therapy or cell therapy may comprise administering a chimeric antigen expressing T-cell (CAR-T), T-cell receptor (TCR), natural killer cell (NK), or dendritic cell (DC) therapy to the subject. The engineered cell therapy or cell therapy may comprise administering exogenously expanding immune cells to the subject.

The term "subject" or "patient" as used herein refers to any individual to which the subject methods are performed. Preferably, the patient or subject is human, although as will be appreciated by those in the art, the patient or subject may be an animal Thus, other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definitions of patient and subject.

"Treatment" and "treating" refer to administration or application of a therapeutic agent to a subject or performance of a procedure or modality on a subject for the purpose of obtaining a therapeutic benefit of a disease or health-related condition. For example, a treatment may include administration chemotherapy, immunotherapy, radiotherapy, performance of surgery, or any combination thereof.

The methods described herein are useful in treating cancer. Generally, the terms "cancer" and "cancerous" refer to or describe the physiological condition in mammals that is typically characterized by unregulated cell growth. More specifically, cancers that are treated in connection with the methods provided herein include, but are not limited to, solid tumors, metastatic cancers, and/or non-metastatic cancers. In certain embodiments, the cancer may originate in the lung, kidney, bladder, blood, bone, bone marrow, brain, breast, colon, esophagus, duodenum, small intestine, large intestine, colon, rectum, anus, gum, head, liver, nasopharynx, neck, ovary, pancreas, prostate, skin, stomach, testis, tongue, or uterus.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 2A-C: Abscopal effect in a fibrolamellar hepatocellular carcinoma patient: FIG. 2A, The patient was treated with SBRT high dose (50 Gy total in 4 fractions) directed towards the smaller tumor circled in the upper left image plus systemic Ipilimumab (an anti-CTLA4 drug). FIG. 2B, The larger abscopal tumor that received low dose XRT scatter significantly responded and shrank as measured after 8 month period. FIG. 2C, However, three other tumors in the lung that did not get scatter radiation did not respond at all, demonstrating the need for low dose XRT to open up or sensitize the tumor. Additionally, the data demonstrate that the high dose and low dose can be delivered at the same time.

FIGS. 3A-C: High dose XRT with low dose XRT and checkpoint blockade achieved significant survival in our preclinical murine model and proved that the systemic anti-tumor response is immune mediated.

FIGS. 4A-B: FIG. 4B, Low dose XRT favors M1 macrophage polarization. Spleens (spl), tumor draining lymph nodes (dLNs) and tumor infiltrating leukocytes (TILs) were harvested 48 h post low dose XRT and subjected to flow cytometric analysis.

FIG. 5: Low-dose radiation reduces TGF-B expression. Mice with bilaterally established 344SQ lung adenocarcinoma tumors were administered high-dose radiation (12 Gy×3, "High XRT only"), optionally in combination with low-dose radiation (1 Gy×2) administered to secondary tumors ("High+Low XRT"). Where specified, anti-PD1 (α-PD1) and anti-CTLA-4 (α-CTLA-4) were given systemically in combination with the XRT. Control mice ("Ctrl") are also shown. *P≤0.05

DESCRIPTION OF ILLUSTRATIVE EMBODIMENTS

In some aspects, improved radiotherapies are provided that can be advantageously used to treat a disease in a subject, such as a cancer. As described herein, lower (e.g., sub-clinical) dosages of XRT may be advantageously administered to a subject in combination with higher dose XRT. For example, a higher dose XRT may be administered to a primary tumor, and a lower dose (e.g., sub-clinical dose) XRT may be separately administered to secondary or metastatic tumors. Without wishing to be bound by any theory, data provided herein supports the idea that low dose XRT (e.g., 20-160 cGy per fraction, which is a sub-clinical dose as compared to dosages used for local control) can be used to draw in or attract and activate immune cells, such as T cells, into tumors and result in improved cancer cell killing. Due to the improved systemic immune effects resulting from the low dose XRT, the radiotherapy may be used in combination with an immunotherapy such as, e.g., engineered cell therapies such as CAR-T cells. Without wishing to be bound by any theory, the data provided supports the idea that a radiotherapy described herein (e.g., including a low dose XRT or sub-clinical dose XRT) may be used to enhance the action of one or more engineered cell therapies such as CAR-T cells, for example, by helping the engineered cells infiltrate solid tumors, which is currently a major obstacle to the clinical effectiveness of engineered cell therapies.

I. Radiotherapies

In some aspects, a radiotherapy is repeatedly administered to a subject (e.g., a human subject) at different dosages (e.g., such as a first higher dosage and a subsequent lower dosage), optionally in combination with an anti-cancer therapy such as an immunotherapy, in order to achieve improved therapeutic responses (e.g., an improved anti-cancer response, improved survival, and/or improved abscopal effects, etc.). Radiotherapy is the use of high-energy radiation from x-rays, gamma rays, neutrons, protons, and other sources to kill cancer cells and shrink tumors. Radiotherapy may also be called irradiation and radiation therapy. In some embodiments, the first radiotherapy (e.g., higher dose XRT) is administered to a primary tumor, and the second radiotherapy (e.g., lower dose XRT) is administered to one or more secondary metastases. As shown in the below examples, treating transplanted tumors in mice at one site with stereotactic high dose XRT followed by non-ablative low dose XRT directed towards other systemic tumor sites significantly reduced the growth of secondary tumors and limited metastasis.

In some embodiments, repeated administration of varied dosages of a radiotherapy are administered to a subject to treat a cancer. X-rays, gamma rays, and charged particles are examples of types of radiation used for cancer treatment. The radiation may be delivered by a machine outside the body (external-beam radiation therapy (XRT)), or it may come from radioactive material placed in the body near cancer cells (internal radiation therapy, also called brachytherapy). In some embodiments, the radiotherapy is an XRT, and the radiotherapy may be administered to the subject at a higher dosage to a primary tumor (e.g., XRT ranging from about 20-50 Gy in 3-15 fractions), and a lower dosage (e.g., of about 0.5-1.9 Gy per fraction for a total dose of about 2-12 Gy or 3-12 Gy) may be subsequently administered to secondary tumors in the subject (e.g., 2, 3, 4, 5, 6, 7, 8, 9, 10, 11, 12, 13, 14, or more days during or after the initial administration of the radiotherapy); the subject may receive a second anti-cancer therapy, such as an immunotherapy, in combination with the initial higher dose XRT (e.g., on the same day or within 1, 2, or 3 days). The higher dose XRT may be administered before the lower dose XRT; for example, the higher dose XRT (e.g., SBRT) may be used to prime T cells, and the lower dose XRT may be used to attract or pull in the primed T cells. In some preferred embodiments, the radiotherapy is an XRT; nonetheless, it is envisioned that other radiotherapies may be utilized in combination with or substituted for the XRT. The higher dose XRT may be a Stereotactic Body Radiation Therapy (SBRT).

Radiotherapy includes external-beam radiation therapy; internal radiation therapy (brachytherapy), and systemic radiation therapy. Types of external-beam radiation therapy include: intensity-modulated radiation therapy (IMRT), image-guided radiation therapy (IGRT), tomotherapy, stereotactic radiosurgery, stereotactic body radiation therapy, proton therapy, and other charged particle beams. Systemic radiation therapy uses radioactive substances, such as radioactive iodine or a radiolabeled monoclonal antibody, that travel in the blood and/or to tissues throughout the body to kill cancer cells.

Radiation therapy is a primary therapy for treating patients with various cancers such as, e.g., inoperable localized non-small cell lung carcinoma. However, there is a high rate of local failure, and while it increases median survival, the therapy is often not curative. Standard radiation fractionation provides a daily dose on the order of 1.8-2 Gy, to a final dose of 60-70 Gy. By contrast, a Stereotactic Body Radiation Therapy (SBRT), also referred to as a stereotactic ablative radiotherapy (SABR), is a somewhat newer technique in radiation therapy of lung carcinomas, and can be used to deliver the total radiation dose in 5 or fewer treatments of radiation (hypofractionation). Response rates in clinical trials suggest SBRT could be an important therapeutic advance. This approach may have significant relevance to the endogenous immune response, since lymphocytes are sensitive to even low radiation doses and are cleared rapidly from the radiation field. Standard fractionated radiation treatment may limit the effectiveness of the immune system by constantly removing tumor antigen-specific T cells at the target site. Thus, although standard fractionation has been shown to generate endogenous anti-tumor immune responses, SBRT hypofractionation may in some embodiments provide benefits when combined with an immunotherapy. In traditional external beam radiation therapy coupled with radiosensitizer administration, a beam of high energy X-rays, generated outside the patient by a linear accelerator, is delivered to a tumor. Most body tissue does not absorb or block X-rays, so they progress through the body, constantly releasing energy. When the cancer tumor is within the path of the X-ray, it receives some of that radiation; however, surrounding healthy tissue receives radiation as well. In order to limit the extent of collateral tissue damage, oncologists typically bombard the tumor area with the lowest level of effective radiation from many different points of entrance in an attempt to minimize damage to normal tissues. Even modern external beam radiation systems with improved real-time imaging of the patient anatomy will inevitably treat substantial normal tissue volumes when targeting the tumor.

Other energy sources, such as particle beams contain charged atomic particles. Particle beams have tremendous energy but also high mass and as such they slow down as they encounter body tissue. Particles can be controlled, for example, to release their energy at a specific point in the body. Particle beam therapy uses electrons, neutrons, heavy ions (such as protons, carbon ions and helium); and pi-mesons (also called pions).

Recent approaches to radiotherapy use high-dose radiation with precise focus on the cancerous area, limiting exposure of healthy cells to radiation. Stereotactic Body Radiation Therapy ("SBRT"), uses image-guided, focused high-dose external beam x-ray radiation to irradiate a tumor, often in a single fraction. To avoid the excessive toxicity which can occur to normal tissue, however, many tumors, even when targeted with SBRT, must be irradiated over two to five fractions, each fraction of lower dose than single fraction SBRT. The reduced dose per SBRT fraction may not be adequate to destroy the hypoxic component of the tumor.

Intraoperative Radiation Therapy ("IORT") is the delivery of radiation at the time of surgery using a focused high-dose radiation directed to the site of the cancerous cells. IORT is characterized by a concentrated beam of ionizing radiation to cancerous tumors while the patient is exposed during surgery, i.e., radiation is delivered within an open body cavity. IORT has an advantage of being able to temporarily displace healthy tissue from the path of the radiation beam to reduce the exposure of normal tissues to the radiation and contact the tumor site more directly. Single dose IORT in excess of 8-10 Gy is effective at destroying tumor stem cells and its host-derived microvascular structure, thereby inhibiting DNA repair in the tumor, but hypoxic cells within the tumor may require doses in excess of 20-24 Gy, doses that could exceed normal tissue tolerance.

Various radiotherapy methods that utilize γ-rays or X-rays may be used. In some instances, it is anticipated that as microwaves, proton beam irradiation (U.S. Pat. Nos. 5,760,395 and 4,870,287), or UV-irradiation may be used as a radiotherapy. In some embodiments, directed delivery of radioisotopes to tumor cells may also be used.

As used herein, a "high dose" or "higher dose" radiotherapy or radiation therapy, such as an XRT, refers to a cumulative external irradiation of a patient in a dose of about 10-90 Gy, more preferably about 10-60, 10-50, 10-45, 10-40, 15-40, 15-35, 25-35, 30-40, 10-35, 10-25, 10-20, 15-30 Gy, or about 10, 15, 20, 25, 30, 35, 40 Gy, or any range derivable therein. The high dose radiotherapy may be separated into separate administrations (e.g., 1, 2, 3, or 4 administrations of the radiotherapy over a period of about 1, 2, 3, or 4 days). The higher dose radiotherapy may provide about 1.8-2 Gy per fraction. The high dose radiotherapy or XRT may be delivered, e.g., in 1, 2, 3, 4, or 5 fractions. The high dose radiotherapy may be a SBRT.

As used herein, a "low dose" or "lower dose" radiotherapy or radiation therapy, such as an XRT, refers to a dosage of 0.1-1.9 Gy per fraction, or about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9 Gy per fraction, or any range derivable therein. The low dose radiotherapy may comprise a total dose of about 1-13, 2-12, 1-9, 2-9, 2-10, 1, 2, 3, 4, 5, 6, 7, 8, 9, 10, 11, or 12 Gy, or any range derivable therein. The low dose radiotherapy may be separated into separate administrations (e.g., 1, 2, 3, or 4 administrations of the radiotherapy over a period of about 1, 2, 3, or 4 days). The low dose radiotherapy may provide a dose of 10-170, 10-160, 20-160, 30-140, or 10, 20, 30, 40, 50, 60, 70, 80, 90, 100, 110, 120, 130, 140, 150, 160, or 170 cGy per fraction, or any range derivable therein. In some preferred embodiments, the low dose radiotherapy is a sub-clinical dose of XRT (e.g., 20-190 cGy per fraction, for a total of 2-12 Gy). The low dose radiotherapy or XRT may be delivered, e.g., in 1, 2, 3, 4, or 5 fractions. The lower dose radiotherapy may be a SBRT. In some embodiments, the low dose radiotherapy is administered to a subject (e.g., a human patient), but a higher dose radiotherapy is not administered to the subject; in these embodiments, it may be desirable to administer to the subject a second anti-cancer therapy such as, e.g., an immunotherapy or a checkpoint inhibitor.

Administration of the high dose radiotherapy (e.g., high dose XRT) and low dose radiotherapy (e.g., low dose XRT) may be separated by a period of, e.g., about 1, 2, 3, 4, 5, 6, 7, 8, 9, 10, 11, 12, 13, 14 days, or any range derivable therein, or about 1, 2, 3, 4, 5, 6 or more weeks, or any range derivable therein. In some embodiments, an immunotherapy (e.g., a checkpoint inhibitor immunotherapy) is administered to the subject after a first high dose XRT and before or after a second lower dose XRT.

Radiation therapy may be stereotactic body radiotherapy, or SBRT. Stereotactic radiotherapy uses essentially the same approach as stereotactic radiosurgery to deliver radiation to the target tissue; however, stereotactic radiotherapy generally uses multiple small fractions of radiation as opposed to one large dose, but certain applications of SBRT may still be accomplished with a single fraction. Stereotactic body radiotherapy may be used to treat tumors, e.g., in the brain, lung, liver, pancreas, prostate, spine, as well as other parts of the body.

Radiotherapy may be used for curative, adjuvant, or palliative treatment. Suitable types of radiotherapy include conventional external beam radiotherapy, stereotactic radiation therapy (e.g., Axesse™, Cyberknife, Gamma Knife®, Novalis®, Primatom, Synergy, X-knife, TomoTherapy® or Trilogy®), Intensity-Modulated Radiation Therapy, particle therapy (e.g., proton therapy), brachytherapy, delivery of radioisotopes, intraoperative radiotherapy, Auger therapy, Volumetric modulated arc therapy (VMAT), Virtual simulation, 3-dimensional conformal radiation therapy, and intensity-modulated radiation therapy, etc.

The radiotherapy may be administered in combination with a second anti-cancer therapy, such as an immunotherapy (e.g., an anti-CTLA4 compound or antibody, an anti-OX40 antibody, or an anti-PD-1 antibody). Anti-OX40 antibodies include agonist antibodies, and anti-PD-1 antibodies include an antagonist antibodies, e.g., as described in WO2018150326. In some embodiments, the radiation therapy used is a SBRT. The cancer may be, e.g., an anti-PD-1 resistant cancer. For example, an anti-OX40 ABP (e.g., an agonist antibody) may be administered with a first high dose XRT for the treatment of a cancer (e.g., an anti-PD-1 resistant cancer), and a second lower dose XRT is subsequently administered to the subject (e.g., to a secondary or metastatic tumor). Suitable examples of radiation therapy that may be used include, for example, external beam radiotherapy (EBRT or XRT), teletherapy, brachytherapy, sealed source radiotherapy, systemic radioisotope therapy, and unsealed source radiotherapy. In some embodiments, an anti-PD-1 ABP (e.g., an antagonist antibody) is included in the combination.

II. Combination of Treatments

In some embodiments, the radiotherapies disclosed herein may be administered in combination with a second anticancer therapy to treat a cancer in a patient. For example, a first radiotherapy (e.g., higher dose XRT administered to a primary tumor) may be administered to a patient in combination with an anticancer treatment (e.g., an immunotherapy), and a second radiotherapy (e.g., a lower dose XRT directed to a secondary tumor) may be subsequently administered to a patient (e.g., after the higher dose XRT). It is anticipated that the repeated radiotherapies may be advantageously combined with a variety of immunotherapies such as, e.g., anti-PD1 antibodies or compounds, anti-PD-L1 antibodies or compounds, anti-CTLA-4 antibodies or compounds, OX40 agonists, 4-1BB agonists, anti-TGF-β immunotherapies, a MER-TK-targeted immunotherapy, IDO inhibitors, anti-GITR antibodies or compounds, anti-LAGS antibodies or compounds, anti-TIM3 antibodies or compounds, anti-TIGIT antibodies or compounds, and anti-MERTK antibodies or compounds. Additionally, the second radiotherapy (e.g., lower dose XRT) could be combined with cell therapies, such as CAR-T, T-cell receptor (TCR), Natural killer cells (NK), dendritic cells (DC), which can provide therapeutic responses in liquid tumors but are generally unable to penetrate into solid tumors, due to stromal inhibitory barriers. It is anticipated that the repeated radiotherapies described herein (e.g., a first higher dose XRT administered to a primary tumor, followed by a lower dose XRT administered to one or more secondary tumors) may facilitate the expansion of XRT's role from local therapy to systemic immunological therapy.

The methods and compositions, including combination therapies, may enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. A tissue, tumor, or cell can be contacted with one or more compositions or pharmacological formulation(s) comprising one or more of the agents or by contacting the tissue, tumor, and/or cell with two or more distinct compositions or formulations. Also, it is contemplated that such repeated radiotherapies (e.g., a higher dose XRT followed by a lower dose XRT) in combination with an immunotherapy may be used in conjunction with a chemotherapy and/or surgical therapy.

A first radiotherapy (e.g., a low dose XRT) may be administered in combination with a first anticancer treatment, such as an immunotherapy. The administrations may be in intervals ranging from concurrently to minutes to days. One would generally ensure that a significant period of time did not expire between the time of the first radiotherapy and the first anticancer treatment, such that the two treatments would still be able to exert an advantageously combined effect on the patient. In such instances, it is contemplated that one may provide a patient with the first radiotherapy and a first immunotherapy within about 12 to 24 or 72 h or within several days (2, 3, 4, 5, 6, or 7). A second radiotherapy may be subsequently administered to the subject within several weeks (such as about 1, 2, 3, 4, 5, 6, 7, or 8 weeks) after the first radiotherapy. Although in some instances it may be preferable to administer an immunotherapy before, concurrently with the first radiotherapy, or after the first radiotherapy. In some embodiments, a high dose radiotherapy is administered before a low dose radiotherapy.

Administration of any compound or therapy of the present invention to a patient will follow general protocols for the administration of such compounds, taking into account the toxicity, if any, of the agents. Therefore, in some embodiments there is a step of monitoring toxicity that is attributable to combination therapy.

1. Immunotherapy

In some preferred embodiments, radiotherapies as described herein are administered in combination with an immunotherapy, and it is anticipated that this combination may be particularly useful due to possible immune-stimulating effects of the radiotherapy. Various immunotherapies are known that may be used in combination with a low dose radiotherapy as disclosed herein, including, e.g., anti-PD1 antibodies or compounds, anti-PD-L1 antibodies or compounds, anti-CTLA-4 antibodies or compounds, anti-TGF-β antibodies, OX40 agonists, 4-1BB agonists, IDO inhibitors, anti-GITR antibodies or compounds, anti-LAG3 antibodies or compounds, anti-TIM3 antibodies or compounds, anti-TIGIT antibodies or compounds, and anti-MERTK antibodies or compounds, an oncolytic virus immunotherapy, intratumoral injections; immunotherapies targeting STING, NLRP3, TLR9, CPG, TLR4, TLR7/8, OX40, or MER-TK; an anti-CTLA-4, anti-PD1, anti-PDL1, or anti-CD40 immunotherapy; FLT-3-ligand immunotherapies, and/or IL-2 cytokine immunotherapies. Additionally, the second radiotherapy (e.g., lower dose XRT) could be combined with cell therapies, such as CAR-T, T-cell receptor (TCR), Natural killer cells (NK), or dendritic cells (DC). In some embodiments, the immunotherapy is alemtuzumab, atezolizumab, ipilimumab, nivolumab, ofatumumab, pembrolizumab, or rituximab.

The skilled artisan will understand that additional immunotherapies may be used in combination or in conjunction with methods of the invention. In the context of cancer treatment, immunotherapeutics typically rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell typically must bear some marker that is amenable to targeting, i.e., is not present on the majority of other cells. Many tumor markers exist and any of these may be suitable for targeting in the context of the present invention. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules that may be used include: cytokines, such as IL-2, IL-4, IL-12, IL-15, GM-CSF, gamma-IFN, chemokines, such as MIP-1, MCP-1, IL-8, and growth factors, such as FLT3 ligand.

Examples of immunotherapies currently under investigation or in use include immune adjuvants, e.g., *Mycobacterium bovis, Plasmodium falciparum*, dinitrochlorobenzene, and aromatic compounds (U.S. Pat. Nos. 5,801,005 and 5,739,169; Hui and Hashimoto, Infection Immun., 66(11): 5329-5336, 1998; Christodoulides et al., Microbiology, 144 (Pt 11):3027-3037, 1998; cytokine therapy, e.g., interferons α, β, and γ, IL-1, GM-CSF, and TNF (Bukowski et al., Clinical Cancer Res., 4(10):2337-2347, 1998; Davidson et al., J. Immunother., 21(5):389-398, 1998; Hellstrand et al., Acta Oncologica, 37(4):347-353, 1998); gene therapy, e.g., TNF, IL-1, IL-2, and p53 (Qin et al., Proc. Natl. Acad. Sci. USA, 95(24):14411-14416, 1998; Austin-Ward and Villaseca, Revista Medica de Chile, 126(7):838-845, 1998; U.S. Pat. Nos. 5,830,880 and 5,846,945); and monoclonal antibodies, e.g., anti-CD20, anti-ganglioside GM2, and anti-γ185 (Hanibuchi et al., Int. J. Cancer, 78(4):480-485, 1998; U.S. Pat. No. 5,824,311). It is contemplated that one or more anti-cancer therapies may be employed with the antibody therapies described herein.

In some embodiment, the immune therapy could be adoptive immunotherapy, which involves the transfer of autologous antigen-specific T cells generated ex vivo. The T cells used for adoptive immunotherapy can be generated either by expansion of antigen-specific T cells or redirection of T cells through genetic engineering. Isolation and transfer of tumor specific T cells has been shown to be successful in treating melanoma. Novel specificities in T cells have been successfully generated through the genetic transfer of transgenic T cell receptors or chimeric antigen receptors (CARs). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. CARs have successfully allowed T cells to be redirected against antigens expressed at the surface of tumor cells from various malignancies including lymphomas and solid tumors.

In one embodiment, the present application provides for a combination therapy for the treatment of cancer wherein the combination therapy comprises adoptive T cell therapy and a checkpoint inhibitor. In one aspect, the adoptive T cell therapy comprises autologous and/or allogenic T-cells. In another aspect, the autologous and/or allogenic T-cells are targeted against tumor antigens.

2. Chemotherapy

In some embodiments, a chemotherapeutic may be administered to the subject in combination with the radiotherapies described herein. A wide variety of chemotherapeutic agents may be used in accordance with the present invention. In some embodiments, a chemotherapeutic may be chosen with exerts reduced adverse effects on the immune system of a subject with a cancer. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. In some embodiments, a chemotherapy may be administered to a subject before or after the radiotherapies described herein (wherein the radiotherapy is optionally administered in combination with an immunotherapy).

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammall and calicheamicin omegall); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PS Kpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DFMO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

3. Surgery

The radiotherapies described herein may be combined with a surgery to treat or remove a cancer. Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present invention, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

4. Other Agents

It is contemplated that other agents may be used in combination with certain aspects of the present invention to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as an EGFR antibody (e.g., c225), could be used in combination with a radiotherapy as disclosed herein.

III. Cancers

It is generally anticipated that the radiotherapy methods disclosed herein may be used to treat any cancer that may be amenable to treatment with a radiotherapy. For example, in some embodiments, the cancer is a lung cancer (e.g., NSCLC).

In some embodiments, a radiation therapy (e.g., a high dose XRT, followed by a lower dose XRT to secondary tumors) as disclosed herein is administered to treat a primary cancer. In some embodiments, while the radiation therapy may not be part of the main treatment for a cancer type, it may nonetheless be used to treat tumors that have spread to other parts of the body (e.g., metastatic tumors that have spread to the brain, spinal fluid, or testicles, or lung, etc.). The cancer may specifically be of the following histological type, though it is not limited to these: neoplasm, malignant; carcinoma; non-small cell lung cancer; renal cancer; renal cell carcinoma; clear cell renal cell carcinoma; lymphoma; blastoma; sarcoma; carcinoma, undifferentiated; meningioma; brain cancer; oropharyngeal cancer; nasopharyngeal cancer; biliary cancer; pheochromocytoma; pancreatic islet cell cancer; Li-Fraumeni tumor; thyroid cancer; parathyroid cancer; pituitary tumor; adrenal gland tumor; osteogenic sarcoma tumor; neuroendocrine tumor; breast cancer; lung cancer; head and neck cancer; prostate cancer; esophageal cancer; tracheal cancer; liver cancer; bladder cancer; stomach cancer; pancreatic cancer; ovarian cancer; uterine cancer; cervical cancer; testicular cancer; colon cancer; rectal cancer; skin cancer; giant and spindle cell carcinoma; small cell carcinoma; small cell lung cancer; papillary carcinoma; oral cancer; oropharyngeal cancer; nasopharyngeal cancer; respiratory cancer; urogenital cancer; squamous cell carcinoma; lymphoepithelial carcinoma; basal cell carcinoma; pilomatrix carcinoma; transitional cell carcinoma; papillary transitional cell carcinoma; adenocarcinoma; gastrointestinal cancer; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma with squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; lentigo maligna melanoma; acral lentiginous melanoma; nodular melanoma; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; an endocrine or neuroendocrine cancer or hematopoietic cancer; pinealoma, malignant; chordoma; central or peripheral nervous system tissue cancer; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; B-cell lymphoma; malignant lymphoma; Hodgkin's disease; Hodgkin's; low grade/follicular non-Hodgkin's lymphoma; paragranuloma; malignant lymphoma, small lymphocytic; malignant lymphoma, large cell, diffuse; malignant lymphoma, follicular; mycosis fungoides; mantle cell lymphoma; Waldenstrom's macroglobulinemia; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; chronic lymphocytic leukemia (CLL); acute lymphoblastic leukemia (ALL); Hairy cell leukemia; chronic myeloblastic leukemia; and/or hairy cell leukemia.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Low Dose XRT Combinations Result in Improved Treatment of Lung Cancer

Figure 1:
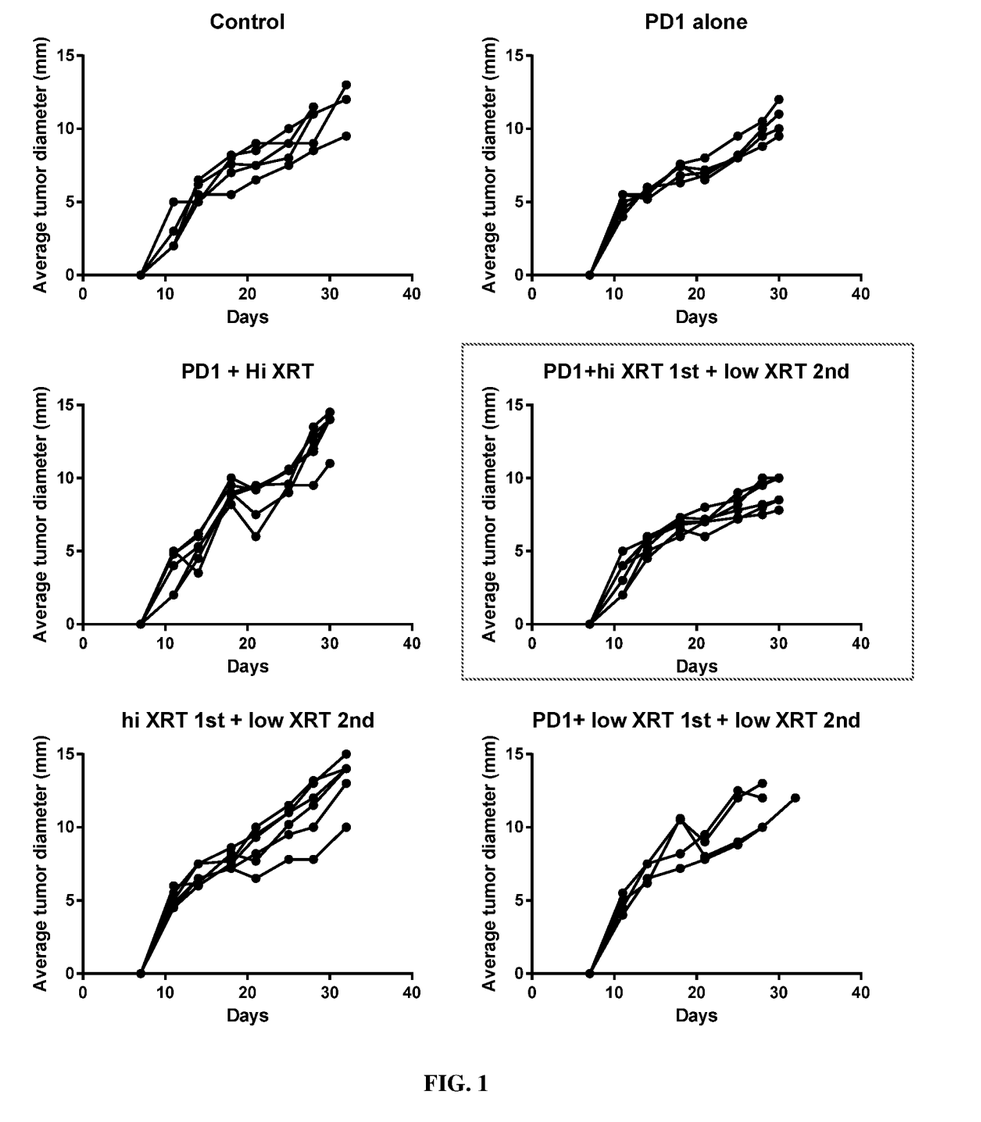
FIG. 1: High dose XRT to primary tumors followed by low dose XRT to secondary tumors promotes abscopal effects and limits the growth of secondary tumors. Abscopal model was established in 129/Sv mice by injecting 344SQ cells in the right hind leg (primary tumor) followed by injecting left hind leg (secondary abscopal tumors) 4 days later. When primary tumors reached around 7 mm in diameter they were irradiated locally with high dose XRT (12 Gy×3) for a total dose of 36 Gy. 4 days after the last high dose of XRT, ad secondary tumors were irradiated with 1 Gy×2 for a total low dose of 2 Gy. Tumors were measured twice a week using calipers and average tumor diameters were reported for the secondary tumors as shown. Systemic immunotherapy with anti-PD1 antibody (200 µg/injection) was administered by intraperitoneal injection (i.p.) twice a week for a total of 4 injections starting concurrently with high dose XRT.

The abscopal model was established in 129/Sv mice by injecting 344SQ cells in the right hind leg (primary tumor) followed by injecting left hind leg (secondary abscopal tumors) 4 days later. When primary tumors reached around 7 mm in diameter they were irradiated locally with high dose XRT (12 Gy×3) for a total dose of 36 Gy. 4 days after the last high dose of XRT, secondary tumors were irradiated with 1 Gy×2 for a total low dose of 2 Gy. Tumors were measured twice a week using calipers and average tumor diameters were reported for the secondary tumors as shown above. Systemic immunotherapy with anti-PD1 antibody (200 μg/injection) was administered i.p. twice a week for a total of 4 injections starting concurrently with high dose XRT. The results indicated that high dose XRT to primary tumors followed by low dose XRT to secondary tumors promotes abscopal effects and limits the growth of secondary tumors. Results are shown in FIG. 1.

Figure 2A:
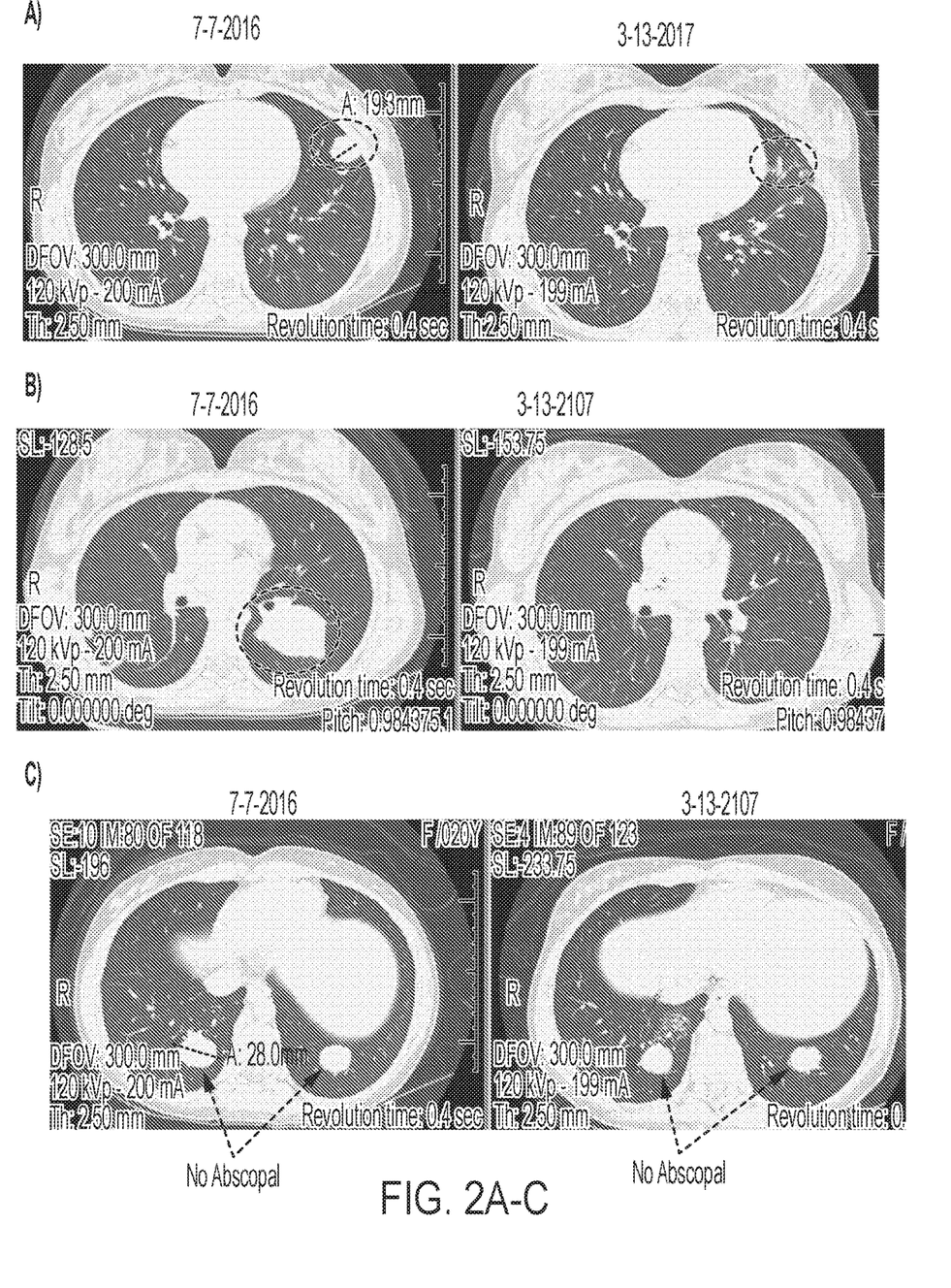

Abscopal effects were also observed in a fibrolamellar hepatocellular carcinoma patient, as follows. As shown in FIG. 2A, the patient was treated with SBRT high dose (50 Gy total in 4 fractions) directed towards the smaller tumor circled in the upper left image plus systemic Ipilimumab (anti-CTLA4 drug). As shown in FIG. 2B, the larger abscopal tumor that received low dose XRT scatter significantly responded and shrank as measured after 8 month period. As shown in FIG. 2C, the three other tumors in the lung that did not get scatter radiation did not respond at all, and these results demonstrate the need for low dose XRT to open up the tumor. Additionally, this demonstrated that the high dose and low dose can be delivered at the same time. Results are shown in FIGS. 2A-C.

Figure 3A:
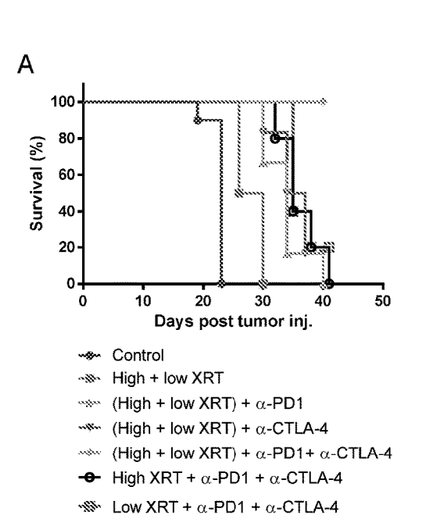
FIG. 3A, Tumors were bilaterally established as in FIG. 1. Primary tumors were irradiated with high dose XRT for antigen spreading and T-cell priming, while secondary tumors were irradiated with low dose XRT to modulate the stroma and generate a welcoming environment for T-cells and NK cells. Anti-PD1 and anti-CTLA-4 were administered twice/week for 2 weeks total.
Figure 3B:
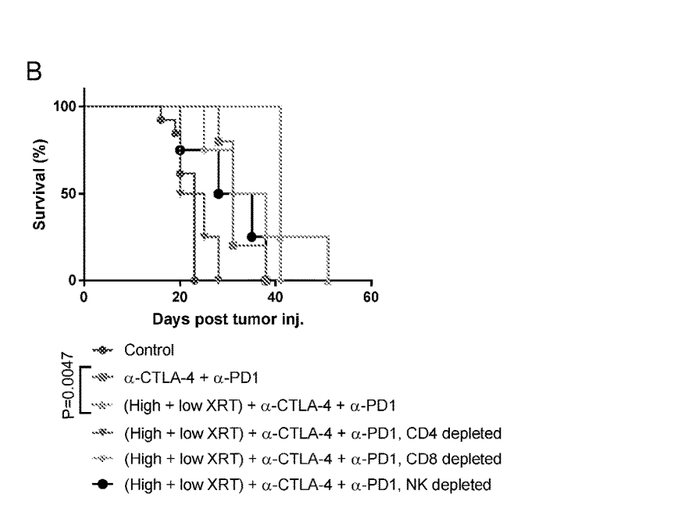
FIG. 3B, Immune cell depletion studies demonstrating that CD4+ T-cells and NK cells were indispensable for the observed immune-mediated anti-tumor effect.
Figure 3C:
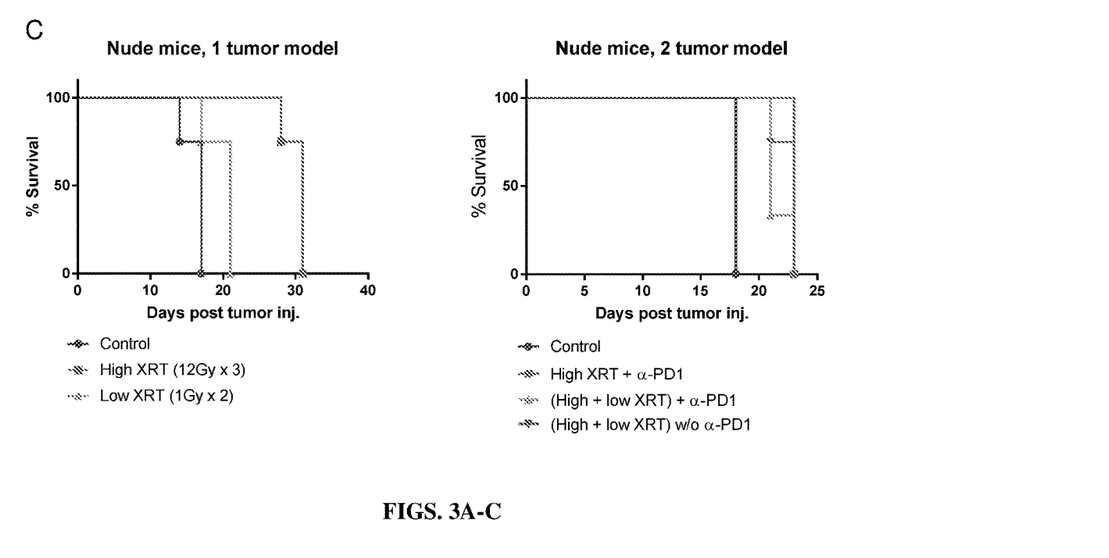
FIG. 3C, High dose and low dose anti-tumor XRT efficacy tested in nude mice lacking functional T-cells; the High+Low XRT efficacy with or without anti-PD1 was lost with the lack of intact immunity.

High dose XRT was combined with low dose XRT and checkpoint blockade achieved significant survival in our preclinical murine model and proved that the systemic anti-tumor response is immune mediated. As shown in FIG. 3A, Tumors were bilaterally established as in FIG. 1. Primary tumors were irradiated with high dose XRT for antigen spreading and T-cell priming, while secondary tumors were irradiated with low dose XRT to modulate the stroma and generate a welcoming environment for T-cells and NK cells. Anti-PD1 and anti-CTLA-4 were administered twice/week for 2 weeks total. As shown in FIG. 3B, Immune cell depletion studies demonstrating that CD4+ T-cells and NK cells were indispensable for the observed immune-mediated anti-tumor effect. As shown in FIG. 3C, High dose and low dose anti-tumor XRT efficacy tested in nude mice lacking functional T-cells; The High+Low XRT efficacy with or without anti-PD1 was lost with the lack of intact immunity.

Figure 4A:
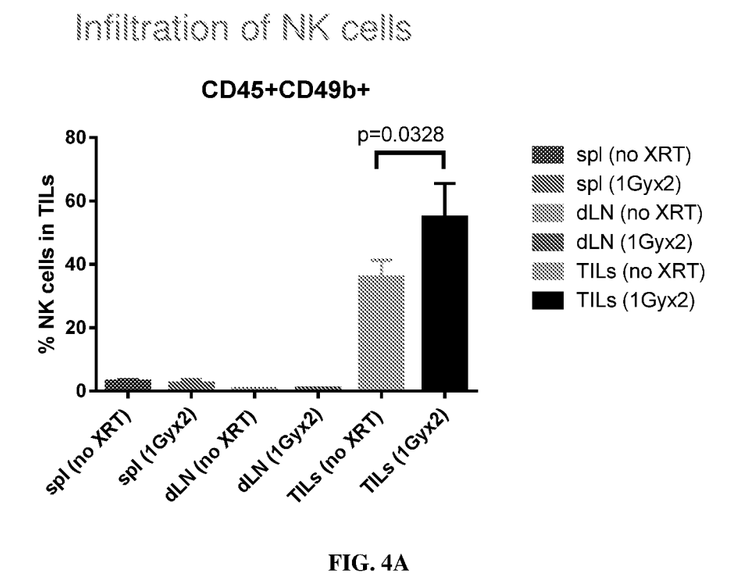
FIG. 4A, Low dose XRT enhances NK infiltration into tumors.
Figure 4B:
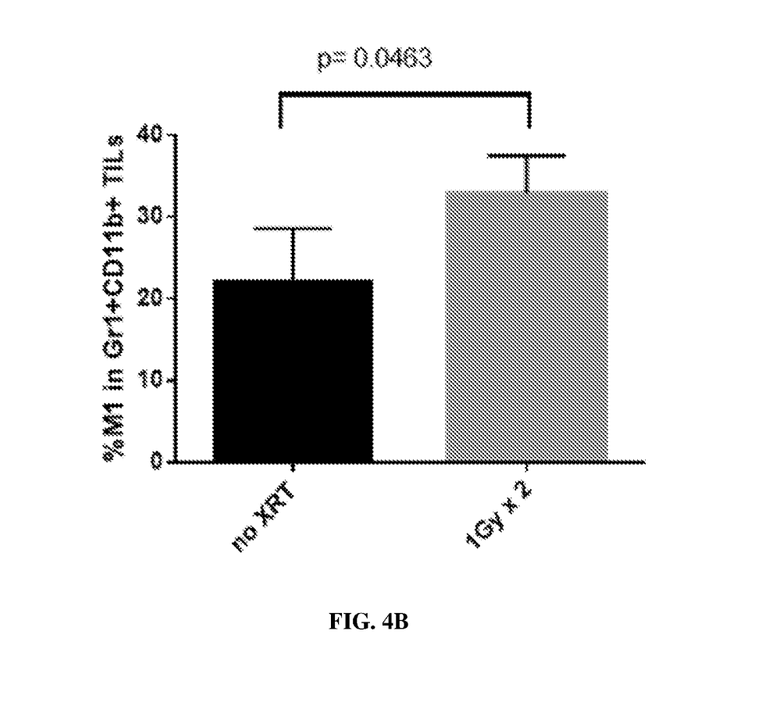

As shown in FIG. 4A, Low dose XRT enhances NK infiltration into tumors. As shown in FIG. 4B, Low dose XRT favors M1 macrophage polarization. Spleens (spl), tumor draining lymph nodes (dLNs) and tumor infiltrating leukocytes (TILs) were harvested 48 h post low dose XRT and subjected to flow cytometric analysis as shown.

Example 2

Low-Dose Radiation Reduces TGF-β Expression

Figure 5:
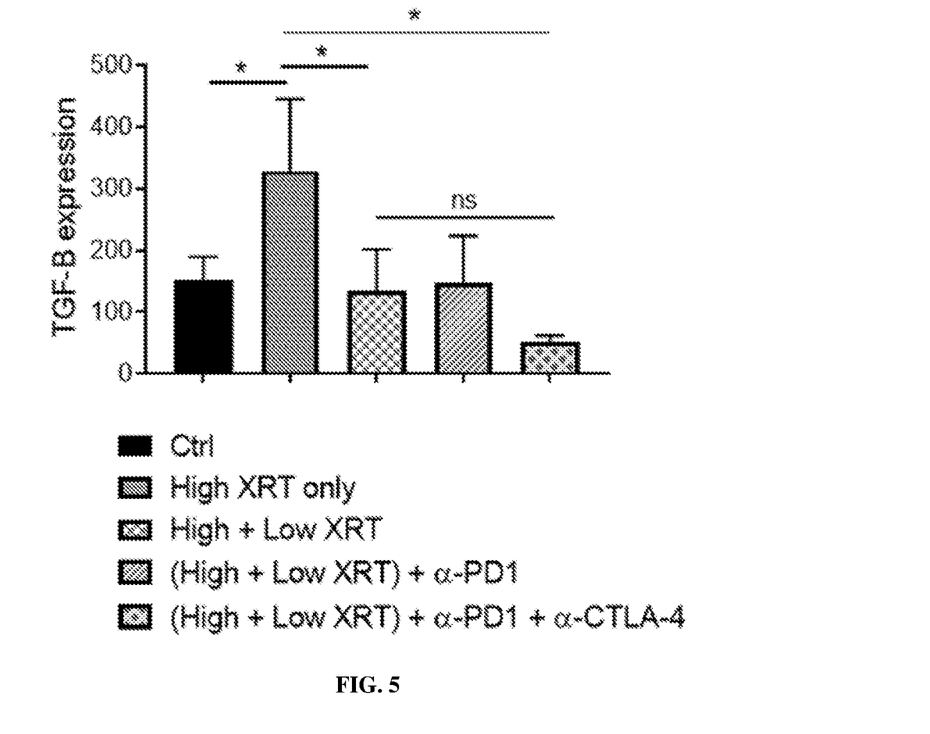

344SQ lung adenocarcinoma tumors were bilaterally established in 129 Sv/Ev mice. Primary tumors received high-dose radiation (12 Gy×3), optionally in combination with low-dose radiation (1 Gy×2) administered to secondary tumors. An anti-PD1 antibody (BMS, 200 μg/injection) and/or an anti-CTLA-4 antibody (BMS, 50 μg/injection) were given systemically in combination with XRT in select mice. TILs were collected from secondary tumors, RNA isolated, and TGF-B expression level was quantitated with RT-PCR (using the method described in Cai et al., 2019). A student t-test was used to compare the groups. Results are shown in FIG. 5. Low-dose radiation was observed to reduce TGF-β expression in the secondary tumors.

Example 3

Low Dose XRT and High Dose XRT Combinations for the Treatment of Patients

Patients with stage 4 solid tumors (lung cancer or melanoma) that progressed on anti-PD1 therapy were selected for a clinical trial. These patients were treated with high dose XRT (50 Gy in 4 fractions), along with low dose XRT (1.4 Gy×5) administered to secondary tumors.

Figure 6:
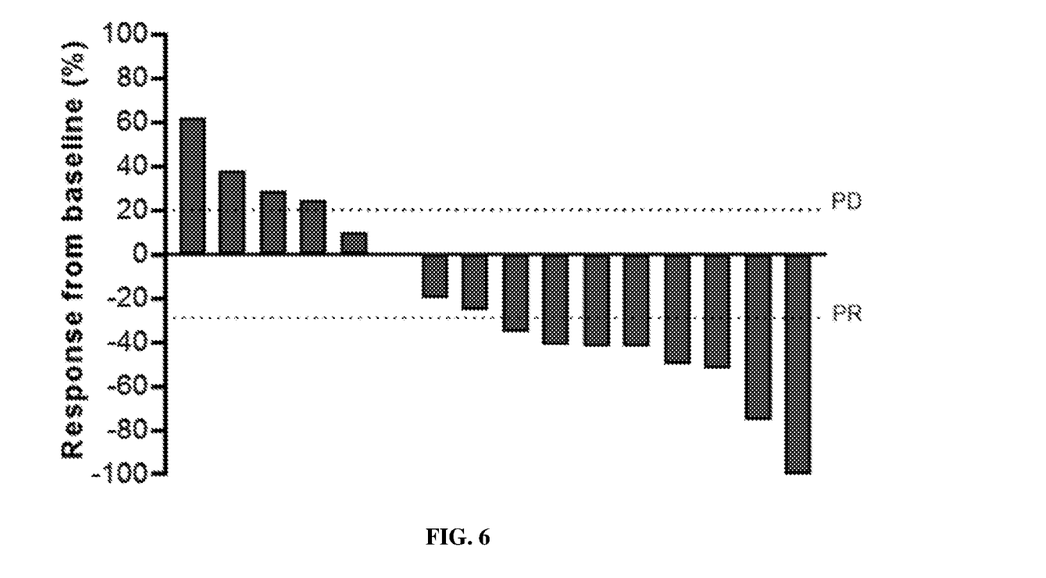
FIG. 6: Clinical response rates per RECIST criteria of RadScopal™ treated lesions. Objective response rate (ORR): 50% (8/16) (CR+PR). Disease control rate (DCR): 75% (12/16) (CR+PR+SD).

Objective response rate (ORR) of the lesions with low dose XRT were observed to be: 50% (8/16) (CR+PR). Disease control rate (DCR) was observed to be: 75% (12/16) (CR+PR+SD). Objective response rate, or ORR, is the proportion of patients in a trial whose tumor is destroyed or significantly reduced by a drug. ORR is generally defined as the sum of complete responses ("CR" or patients with no detectable evidence of a tumor over a specified time period) and partial responses ("PR" or patients with a decrease<30% in tumor size over a specified time period). "SD" refers to subjects or patients with stable disease. Clinical response rates per response evaluation criteria in solid tumors (RECIST) (Eisenhauer et al., 2009) of RadScopal™ treated lesions in these patients are shown in FIG. 6. Without wishing to be bound by any theory, the results are consistent with the idea that the high dose XRT can prime tumors (50 Gy in 4 fractions) and the low dose XRT (1.4 Gy×5) can help attract or pull in the newly primed T cells.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,870,287
U.S. Pat. No. 5,739,169
U.S. Pat. No. 5,760,395
U.S. Pat. No. 5,801,005

U.S. Pat. No. 5,824,311
U.S. Pat. No. 5,830,880
U.S. Pat. No. 5,846,945
WO2018150326
Austin-Ward and Villaseca, Revista Medica de Chile, 126 (7):838-845, 1998.
Bukowski et al., Clinical Cancer Res., 4(10):2337-2347, 1998.
Cai et al., Cancer Res Treat. 51(1):252-266, 2019
Christodoulides et al., Microbiology, 144(Pt 11):3027-3037, 1998.
Davidson et al., J. Immunother., 21(5):389-398, 1998.
Eisenhauer et al., Eur J Cancer. 45(2):228-47, 2009.
Hanibuchi et al., Int. J. Cancer, 78(4):480-485, 1998.
Hellstrand et al., Acta Oncologica, 37(4):347-353, 1998.
Hui and Hashimoto, Infection Immun., 66(11):5329-5336, 1998.
Qin et al., Proc. Natl. Acad. Sci. USA, 95(24):14411-14416, 1998.

The invention claimed is:

1. A method of treating a cancer in a mammalian subject comprising: administering a first radiotherapy to the subject, wherein the radiotherapy comprises a dose of from about 10 cGy to about 170 cGy per fraction, in combination with:
a second radiotherapy, wherein the second radiotherapy is a higher dose than the first radiotherapy;
wherein the first radiotherapy is administered to the subject after the second radiotherapy;
wherein the second radiotherapy is administered to a primary tumor in the mammalian subject, and
wherein the first radiotherapy is administered to a secondary tumor or a metastatic tumor in the mammalian subject.

2. The method of claim 1, wherein the first radiotherapy is an external-beam radiation therapy (XRT).

3. The method of claim 2, wherein the first radiotherapy comprises administering a dosage of 20-160 cGy per fraction or per day.

4. The method of claim 1, wherein the first radiotherapy comprises administering a final dose of about 0.1-12 Gy.

5. The method of claim 4, wherein the first radiotherapy comprises administering a final dose of about 1-9 Gy.

6. The method of claim 1 wherein the second radiotherapy comprises administering a final dose of from about 20 to about 80 Gy; wherein the second radiotherapy is an external-beam radiation therapy (XRT).

7. The method of claim 6, wherein the second radiotherapy comprises administering a final dose of from about 60 Gy to about 70 Gy.

8. The method of claim 1, wherein the first radiotherapy is administered to the subject from about 3 days to about 3 months, or from about 1-4 weeks after the second radiotherapy.

9. The method of claim 1, wherein the method further comprises administering an immunotherapy to the subject.

10. The method of claim 9, wherein the immunotherapy is an antibody or comprises an antibody variable domain.

11. The method of claim 10, wherein the immunotherapy is an anti-PD1 immunotherapy, an anti-PD-L1 immunotherapy, an anti-CTLA-4 immunotherapy, an anti-TGF-β immunotherapy, an OX40 agonist, a 4-1BB agonist, an IDO inhibitor, an anti-GITR immunotherapy, an anti-LAG3 immunotherapy, an anti-TIM3 immunotherapy, an anti-TIGIT immunotherapy, an anti-MERTK immunotherapy, an intratumoral injection, a STING-targeted immunotherapy, a NLRP3-targeted immunotherapy, a TLR9-targeted immunotherapy, a CPG-targeted immunotherapy, a TLR4-targeted immunotherapy, a TLR7/8-targeted immunotherapy, a OX40-targeted immunotherapy, a MER-TK-targeted immunotherapy, an oncolytic virus immunotherapy, an anti-CTLA-4 immunotherapy, an anti-PD1 immunotherapy, an anti-PDL1 immunotherapy, an anti-CD40 immunotherapy, a FLT-3-ligand immunotherapy, or a IL-2 cytokine immunotherapy.

12. The method of claim 11, wherein the immunotherapy is ipilimumab.

13. The method of claim 10, wherein the immunotherapy is alemtuzumab, atezolizumab, ipilimumab, nivolumab, ofatumumab, pembrolizumab, or rituximab.

14. The method of claim 10, wherein the immunotherapy is administered to the subject after the first radiotherapy.

15. The method of claim 9, wherein the immunotherapy is a checkpoint inhibitor.

16. The method of claim 9, wherein the immunotherapy comprises an engineered cell therapy or a cell therapy.

17. The method of claim 16, wherein the immunotherapy comprises administering a chimeric antigen expressing T-cell (CAR-T), T-cell receptor (TCR), natural killer cell (NK), or dendritic cell (DC) therapy to the subject.

18. The method of claim 9, wherein the method further comprises administering a third anti-cancer therapy to the subject, and wherein the third anti-cancer therapy is a chemotherapeutic, an intratumoral injection, or a surgery.

19. The method of claim 9, wherein the method further comprises administering a third anti-cancer therapy to the subject, wherein the third anti-cancer therapy is a chemotherapeutic or a surgery.

20. The method of claim 1, wherein the first radiation therapy results in abscopal effects or systemic immune responses in the subject.

21. The method of claim 1, wherein the subject is a human.

22. The method of claim 1, wherein the cancer is in the lung, head, neck, abdomen, or pelvis.

23. The method of claim 1, wherein the cancer is a lung cancer, a brain cancer, a breast cancer, a head and neck cancer, a cervical cancer, prostate cancer, a cancer of the eye, a liver cancer, or a thyroid cancer.

24. The method of claim 1, comprising administering the immunotherapy to the subject.

25. The method of claim 24, wherein the immunotherapy is an antibody or comprises an antibody variable domain.

26. The method of claim 25, wherein the immunotherapy is an anti-PD1 immunotherapy, an anti-PD-L1 immunotherapy, an anti-CTLA-4 immunotherapy, an anti-TGF-β immunotherapy, an OX40 agonist, a 4-1BB agonist, an IDO inhibitor, an anti-GITR immunotherapy, an anti-LAG3 immunotherapy, an anti-TIM3 immunotherapy, an anti-TIGIT immunotherapy, an anti-MERTK immunotherapy, an intratumoral injection, a STING-targeted immunotherapy, a NLRP3-targeted immunotherapy, a TLR9-targeted immunotherapy, a CPG-targeted immunotherapy, a TLR4-targeted immunotherapy, a TLR7/8-targeted immunotherapy, a OX40-targeted immunotherapy, a MER-TK-targeted immunotherapy, an oncolytic virus immunotherapy, an anti-CTLA-4 immunotherapy, an anti-PD1 immunotherapy, an anti-PDL1 immunotherapy, an anti-CD40 immunotherapy, a FLT-3-ligand immunotherapy, or a IL-2 cytokine immunotherapy.

27. The method of claim 26, wherein the immunotherapy is ipilimumab.

28. The method of claim 25, wherein the immunotherapy is alemtuzumab, atezolizumab, ipilimumab, nivolumab, ofatumumab, pembrolizumab, or rituximab.

29. The method of claim 24, wherein the immunotherapy is a checkpoint inhibitor.

30. The method of claim 24, wherein the immunotherapy comprises an engineered cell therapy or a cell therapy.

31. The method of claim 30, wherein the immunotherapy comprises administering a chimeric antigen expressing T-cell (CAR-T), T-cell receptor (TCR), natural killer cell (NK), or dendritic cell (DC) therapy to the subject.

32. The method of claim 24, wherein the immunotherapy is administered to the subject after the first radiotherapy.

33. The method of claim 1, wherein the method further comprises administering an engineered cell therapy or a cell therapy to the subject.

34. The method of claim 33, wherein the engineered cell therapy or cell therapy comprises administering a chimeric antigen expressing T-cell (CAR-T), T-cell receptor (TCR), natural killer cell (NK), or dendritic cell (DC) therapy to the subject.

35. The method of claim 34, wherein the engineered cell therapy or a cell therapy comprises administering exogenously expanding immune cells to the subject.

36. A method of treating a cancer in a mammalian subject comprising: administering a first radiotherapy to the subject, wherein the radiotherapy comprises a dose of from about 10 cGy to about 170 cGy per fraction, in combination with:
a second radiotherapy, wherein the second radiotherapy is a higher dose than the first radiotherapy,
wherein the second radiotherapy is an external-beam radiation therapy (XRT);
and wherein the second radiotherapy comprises administering a final dose of from about 50 Gy to about 70 Gy;
wherein the second radiotherapy is administered to a primary tumor in the mammalian subject, and
wherein the first radiotherapy is administered to a secondary tumor or a metastatic tumor in the mammalian subject.

37. The method of claim 36, wherein the first radiotherapy is an external-beam radiation therapy (XRT).

38. The method of claim 37, wherein the first radiotherapy comprises a dosage of 20-160 cGy per fraction or per day.

39. The method of claim 36, wherein the first radiotherapy comprises administering a final dose of about 0.1-12 Gy.

40. The method of claim 39, wherein the first radiotherapy comprises administering a final dose of about 1-9 Gy.

41. The method of claim 36, wherein the first radiotherapy is administered to the subject after the second radiotherapy.

42. The method of claim 41, wherein the first radiotherapy is administered to the subject from about 3 days to about 3 months, or from about 1-4 weeks after the second radiotherapy.

43. The method of claim 36, wherein the first radiotherapy is administered to the subject before the second radiotherapy.

44. The method of claim 43, wherein the first radiotherapy is administered to the subject from about 3 days to about 3 months, or from about 1-4 weeks before the second radiotherapy.

45. The method of claim 36, wherein the method further comprises administering an immunotherapy to the subject.

46. The method of claim 45, wherein the immunotherapy is an antibody or comprises an antibody variable domain.

47. The method of claim 46, wherein the immunotherapy is an anti-PD1 immunotherapy, an anti-PD-L1 immunotherapy, an anti-CTLA-4 immunotherapy, an anti-TGF-β immunotherapy, an OX40 agonist, a 4-1BB agonist, an IDO inhibitor, an anti-GITR immunotherapy, an anti-LAG3 immunotherapy, an anti-TIM3 immunotherapy, an anti-TIGIT immunotherapy, an anti-MERTK immunotherapy, an intratumoral injection, a STING-targeted immunotherapy, a NLRP3-targeted immunotherapy, a TLR9-targeted immunotherapy, a CPG-targeted immunotherapy, a TLR4-targeted immunotherapy, a TLR7/8-targeted immunotherapy, a OX40-targeted immunotherapy, a MER-TK-targeted immunotherapy, an oncolytic virus immunotherapy, an anti-CTLA-4 immunotherapy, an anti-PD1 immunotherapy, an anti-PDL1 immunotherapy, an anti-CD40 immunotherapy, a FLT-3-ligand immunotherapy, or a IL-2 cytokine immunotherapy.

48. The method of claim 47, wherein the immunotherapy is ipilimumab.

49. The method of claim 46, wherein the immunotherapy is alemtuzumab, atezolizumab, ipilimumab, nivolumab, ofatumumab, pembrolizumab, or rituximab.

50. The method of claim 46, wherein the immunotherapy is administered to the subject after the first radiotherapy.

51. The method of claim 45, wherein the immunotherapy is a checkpoint inhibitor.

52. The method of claim 45, wherein the immunotherapy comprises an engineered cell therapy or a cell therapy.

53. The method of claim 52, wherein the immunotherapy comprises administering a chimeric antigen expressing T-cell (CAR-T), T-cell receptor (TCR), natural killer cell (NK), or dendritic cell (DC) therapy to the subject.

54. The method of claim 45, wherein the method further comprises administering a third anti-cancer therapy to the subject, and wherein the third anti-cancer therapy is a chemotherapeutic, an intratumoral injection, or a surgery.

55. The method of claim 45, wherein the method further comprises administering a third anti-cancer therapy to the subject, wherein the third anti-cancer therapy is a chemotherapeutic or a surgery.

56. The method of claim 36, wherein the first radiation therapy results in abscopal effects or systemic immune responses in the subject.

57. The method of claim 36, wherein the subject is a human.

58. The method of claim 36, wherein the cancer is in the lung, head, neck, abdomen, or pelvis.

59. The method of claim 36, wherein the cancer is a lung cancer, a brain cancer, a breast cancer, a head and neck cancer, a cervical cancer, prostate cancer, a cancer of the eye, a liver cancer, or a thyroid cancer.

60. The method of claim 36, comprising administering the immunotherapy to the subject.

61. The method of claim 60, wherein the immunotherapy is an antibody or comprises an antibody variable domain.

62. The method of claim 61, wherein the immunotherapy is an anti-PD1 immunotherapy, an anti-PD-L1 immunotherapy, an anti-CTLA-4 immunotherapy, an anti-TGF-β immunotherapy, an OX40 agonist, a 4-1BB agonist, an IDO inhibitor, an anti-GITR immunotherapy, an anti-LAG3 immunotherapy, an anti-TIM3 immunotherapy, an anti-TIGIT immunotherapy, an anti-MERTK immunotherapy, an intratumoral injection, a STING-targeted immunotherapy, a NLRP3-targeted immunotherapy, a TLR9-targeted immunotherapy, a CPG-targeted immunotherapy, a TLR4-targeted immunotherapy, a TLR7/8-targeted immunotherapy, a OX40-targeted immunotherapy, a MER-TK-targeted immunotherapy, an oncolytic virus immunotherapy, an anti-CTLA-4 immunotherapy, an anti-PD1 immunotherapy, an anti-PDL1 immunotherapy, an anti-CD40 immunotherapy, a FLT-3-ligand immunotherapy, or a IL-2 cytokine immunotherapy.

63. The method of claim 62, wherein the immunotherapy is ipilimumab.

64. The method of claim 61, wherein the immunotherapy is alemtuzumab, atezolizumab, ipilimumab, nivolumab, ofatumumab, pembrolizumab, or rituximab.

65. The method of claim 60, wherein the immunotherapy is a checkpoint inhibitor.

66. The method of claim 60, wherein the immunotherapy comprises an engineered cell therapy or a cell therapy.

67. The method of claim 66, wherein the immunotherapy comprises administering a chimeric antigen expressing T-cell (CAR-T), T-cell receptor (TCR), natural killer cell (NK), or dendritic cell (DC) therapy to the subject.

68. The method of claim 60, wherein the immunotherapy is administered to the subject after the first radiotherapy.

69. The method of claim 36, wherein the method further comprises administering an engineered cell therapy or a cell therapy to the subject.

70. The method of claim 69, wherein the engineered cell therapy or cell therapy comprises administering a chimeric antigen expressing T-cell (CAR-T), T-cell receptor (TCR), natural killer cell (NK), or dendritic cell (DC) therapy to the subject.

71. The method of claim 70, wherein the engineered cell therapy or a cell therapy comprises administering exogenously expanding immune cells to the subject.

72. A method of treating a cancer in a mammalian subject comprising: administering a first radiotherapy to the subject, wherein the radiotherapy comprises a dose of from about 10 cGy to about 170 cGy per fraction, in combination with:
a second radiotherapy, wherein the second radiotherapy is a higher dose than the first radiotherapy, and
wherein the first radiotherapy is administered to the subject from about 3 days to about 3 months, or from about 1-4 weeks before the second radiotherapy.

73. The method of claim 72, wherein the first radiotherapy is an external-beam radiation therapy (XRT).

74. The method of claim 73, wherein the first radiotherapy comprises administering a dosage of 20-160 cGy per fraction or per day.

75. The method of claim 72, wherein the first radiotherapy comprises administering a final dose of about 0.1-12 Gy.

76. The method of claim 75, wherein the first radiotherapy comprises administering a final dose of about 1-9 Gy.

77. The method of claim 72, wherein the second radiotherapy comprises administering a final dose of from about 20 to about 80 Gy; wherein the second radiotherapy is an external-beam radiation therapy (XRT).

78. The method of claim 77, wherein the second radiotherapy comprises administering a final dose of from about 60 to about 70 Gy.

79. The method of claim 72, wherein the method further comprises administering an immunotherapy to the subject.

80. The method of claim 79, wherein the immunotherapy is an antibody or comprises an antibody variable domain.

81. The method of claim 80, wherein the immunotherapy is an anti-PD1 immunotherapy, an anti-PD-L1 immunotherapy, an anti-CTLA-4 immunotherapy, an anti-TGF-β immunotherapy, an OX40 agonist, a 4-1BB agonist, an IDO inhibitor, an anti-GITR immunotherapy, an anti-LAG3 immunotherapy, an anti-TIM3 immunotherapy, an anti-TIGIT immunotherapy, an anti-MERTK immunotherapy, an intratumoral injection, a STING-targeted immunotherapy, a NLRP3-targeted immunotherapy, a TLR9-targeted immunotherapy, a CPG-targeted immunotherapy, a TLR4-targeted immunotherapy, a TLR7/8-targeted immunotherapy, a OX40-targeted immunotherapy, a MER-TK-targeted immunotherapy, an oncolytic virus immunotherapy, an anti-CTLA-4 immunotherapy, an anti-PD1 immunotherapy, an anti-PDL1 immunotherapy, an anti-CD40 immunotherapy, a FLT-3-ligand immunotherapy, or a IL-2 cytokine immunotherapy.

82. The method of claim 81, wherein the immunotherapy is ipilimumab.

83. The method of claim 80, wherein the immunotherapy is alemtuzumab, atezolizumab, ipilimumab, nivolumab, ofatumumab, pembrolizumab, or rituximab.

84. The method of claim 80, wherein the immunotherapy is administered to the subject after the first radiotherapy.

85. The method of claim 79, wherein the immunotherapy is a checkpoint inhibitor.

86. The method of claim 79, wherein the immunotherapy comprises an engineered cell therapy or a cell therapy.

87. The method of claim 86, wherein the immunotherapy comprises administering a chimeric antigen expressing T-cell (CAR-T), T-cell receptor (TCR), natural killer cell (NK), or dendritic cell (DC) therapy to the subject.

88. The method of claim 79, wherein the method further comprises administering a third anti-cancer therapy to the subject, and wherein the third anti-cancer therapy is a chemotherapeutic, an intratumoral injection, or a surgery.

89. The method of claim 79, wherein the method further comprises administering a third anti-cancer therapy to the subject, wherein the third anti-cancer therapy is a chemotherapeutic or a surgery.

90. The method of claim 72, wherein the first radiation therapy results in abscopal effects or systemic immune responses in the subject.

91. The method of claim 72, wherein the subject is a human.

92. The method of claim 72, wherein the cancer is in the lung, head, neck, abdomen, or pelvis.

93. The method of claim 72, wherein the cancer is a lung cancer, a brain cancer, a breast cancer, a head and neck cancer, a cervical cancer, prostate cancer, a cancer of the eye, a liver cancer, or a thyroid cancer.

94. The method of claim 72, comprising administering the immunotherapy to the subject.

95. The method of claim 94, wherein the immunotherapy is an antibody or comprises an antibody variable domain.

96. The method of claim 95, wherein the immunotherapy is an anti-PD1 immunotherapy, an anti-PD-L1 immunotherapy, an anti-CTLA-4 immunotherapy, an anti-TGF-β immunotherapy, an OX40 agonist, a 4-1BB agonist, an IDO inhibitor, an anti-GITR immunotherapy, an anti-LAG3 immunotherapy, an anti-TIM3 immunotherapy, an anti-TIGIT immunotherapy, an anti-MERTK immunotherapy, an intratumoral injection, a STING-targeted immunotherapy, a NLRP3-targeted immunotherapy, a TLR9-targeted immunotherapy, a CPG-targeted immunotherapy, a TLR4-targeted immunotherapy, a TLR7/8-targeted immunotherapy, a OX40-targeted immunotherapy, a MER-TK-targeted immunotherapy, an oncolytic virus immunotherapy, an anti-CTLA-4 immunotherapy, an anti-PD1 immunotherapy, an anti-PDL1 immunotherapy, an anti-CD40 immunotherapy, a FLT-3-ligand immunotherapy, or a IL-2 cytokine immunotherapy.

97. The method of claim 96, wherein the immunotherapy is ipilimumab.

98. The method of claim 95, wherein the immunotherapy is alemtuzumab, atezolizumab, ipilimumab, nivolumab, ofatumumab, pembrolizumab, or rituximab.

99. The method of claim 94, wherein the immunotherapy is a checkpoint inhibitor.

100. The method of claim 94, wherein the immunotherapy comprises an engineered cell therapy or a cell therapy.

101. The method of claim 100, wherein the immunotherapy comprises administering a chimeric antigen expressing T-cell (CAR-T), T-cell receptor (TCR), natural killer cell (NK), or dendritic cell (DC) therapy to the subject.

102. The method of claim 94, wherein the immunotherapy is administered to the subject after the first radiotherapy.

103. The method of claim 72, wherein the method further comprises administering an engineered cell therapy or a cell therapy to the subject.

104. The method of claim 103, wherein the engineered cell therapy or cell therapy comprises administering a chimeric antigen expressing T-cell (CAR-T), T-cell receptor (TCR), natural killer cell (NK), or dendritic cell (DC) therapy to the subject.

105. The method of claim 104, wherein the engineered cell therapy or a cell therapy comprises administering exogenously expanding immune cells to the subject.

* * * * *